(12) United States Patent
Getts et al.

(10) Patent No.: US 7,494,789 B2
(45) Date of Patent: Feb. 24, 2009

(54) METHODS FOR AMPLIFICATION OF NUCLEIC ACID SEQUENCES USING STAGGERED LIGATION

(75) Inventors: Robert C. Getts, Collegeville, PA (US); Jaime Boyle, Gilbertsville, PA (US)

(73) Assignee: Genisphere Inc., Montvale, NJ (US)

( * ) Notice: Subject to any disclaimer, the term of this patent is extended or adjusted under 35 U.S.C. 154(b) by 5 days.

(21) Appl. No.: 10/554,374

(22) PCT Filed: May 7, 2004

(86) PCT No.: PCT/US2004/014325
§ 371 (c)(1),
(2), (4) Date: Nov. 16, 2006

(87) PCT Pub. No.: WO2004/101749
PCT Pub. Date: Nov. 25, 2004

(65) Prior Publication Data
US 2007/0072182 A1    Mar. 29, 2007

Related U.S. Application Data

(60) Provisional application No. 60/469,383, filed on May 9, 2003.

(51) Int. Cl.
*C12Q 1/68*    (2006.01)
*C12P 19/34*    (2006.01)

(52) U.S. Cl. ........................... 435/91.1; 435/6; 435/91.2

(58) Field of Classification Search ................ 435/91.1, 435/91.2
See application file for complete search history.

(56) References Cited

U.S. PATENT DOCUMENTS 5,194,370 A    3/1993    Berninger et al.

| | | |
|---|---|---|
| 5,215,899 A | 6/1993 | Dattagupta |
| 6,338,954 B1 | 1/2002 | Gemen |
| 2002/0102589 A1 | 8/2002 | Kiyama et al. |
| 2003/0104432 A1 | 6/2003 | Xu et al. |

FOREIGN PATENT DOCUMENTS

| | | |
|---|---|---|
| WO | 03/029453 | 4/2003 |
| WO | 2005/098044 | 10/2005 |

OTHER PUBLICATIONS

Rajeevan M S et al, Genomics, Academic Press, San Diego, 82:4:491-497 (2003).
Lawson Jonathan N et al, DNA and Cell Biology, 25:11:627-634 (2006).

*Primary Examiner*—Kenneth R. Horlick
(74) *Attorney, Agent, or Firm*—Lerner, David, Littenberg, Krumholz & Mentlik, LLP

(57) ABSTRACT

Methods and kits are provided for producing sense RNA molecules. The sense RNA molecules are prepared by:
  providing a single stranded cDNA molecule having 5' and 3' ends;
  attaching an oligodeoxynucleotide tail to the 3' end of said single stranded cDNA molecule;
  providing a double stranded RNA polymerase promoter having a sense strand and antisense strand, wherein the sense strand comprises a single stranded 3' overhang comprising a sequence complementary to said oligodeoxynucleotide tail;
annealing said double stranded RNA polymerase promoter to said oligodeoxynucleotide tail by complementary base pairing with said 3' overhang sequence;
ligating the 5' end of the antisense strand of said double stranded RNA polymerase promoter to the 3' end of said oligodeoxynucleotide tail; and
initiating RNA transcription using an RNA polymerase which recognizes said double stranded promoter, thus producing a sense RNA molecule (sRNA).

38 Claims, 3 Drawing Sheets

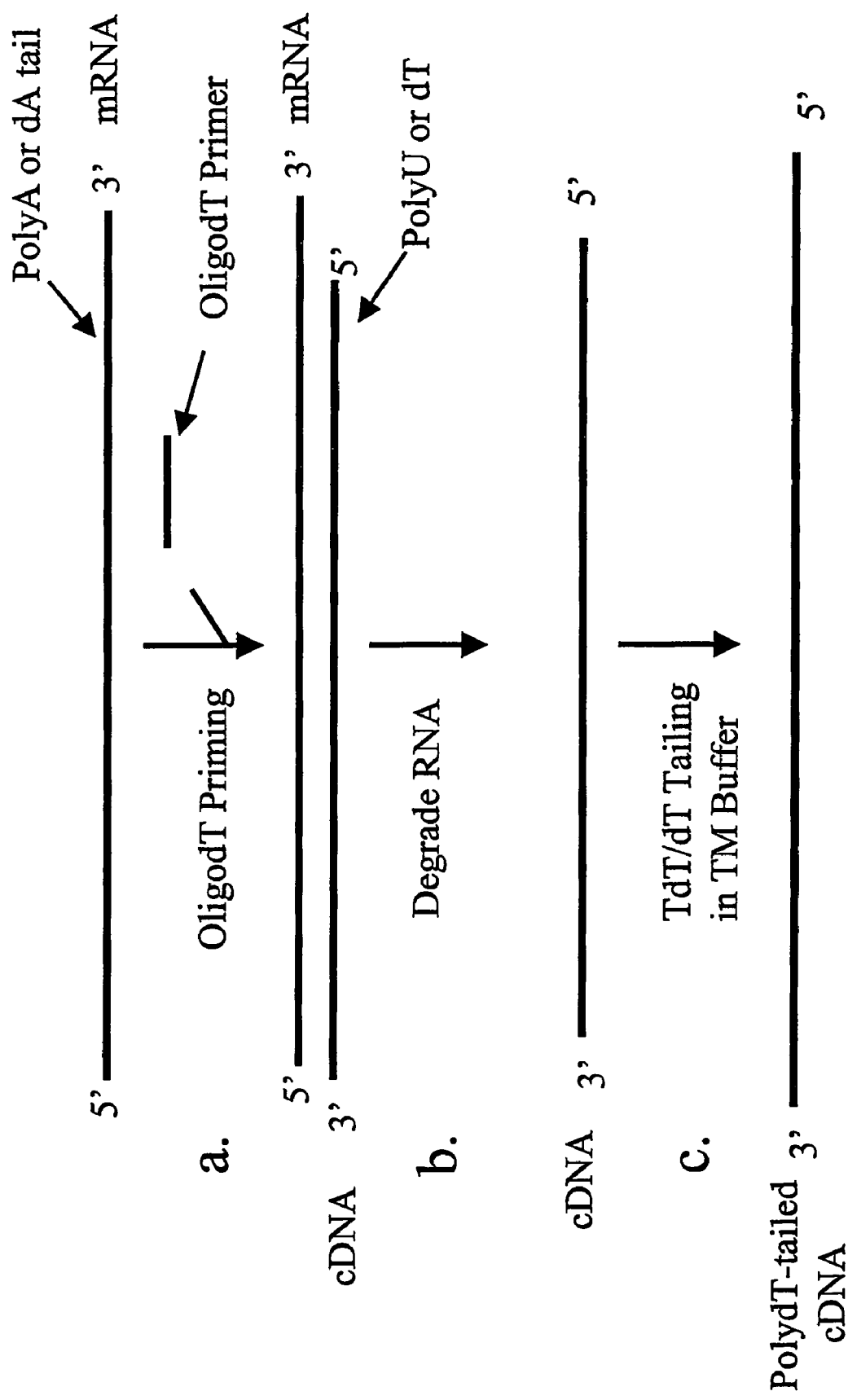

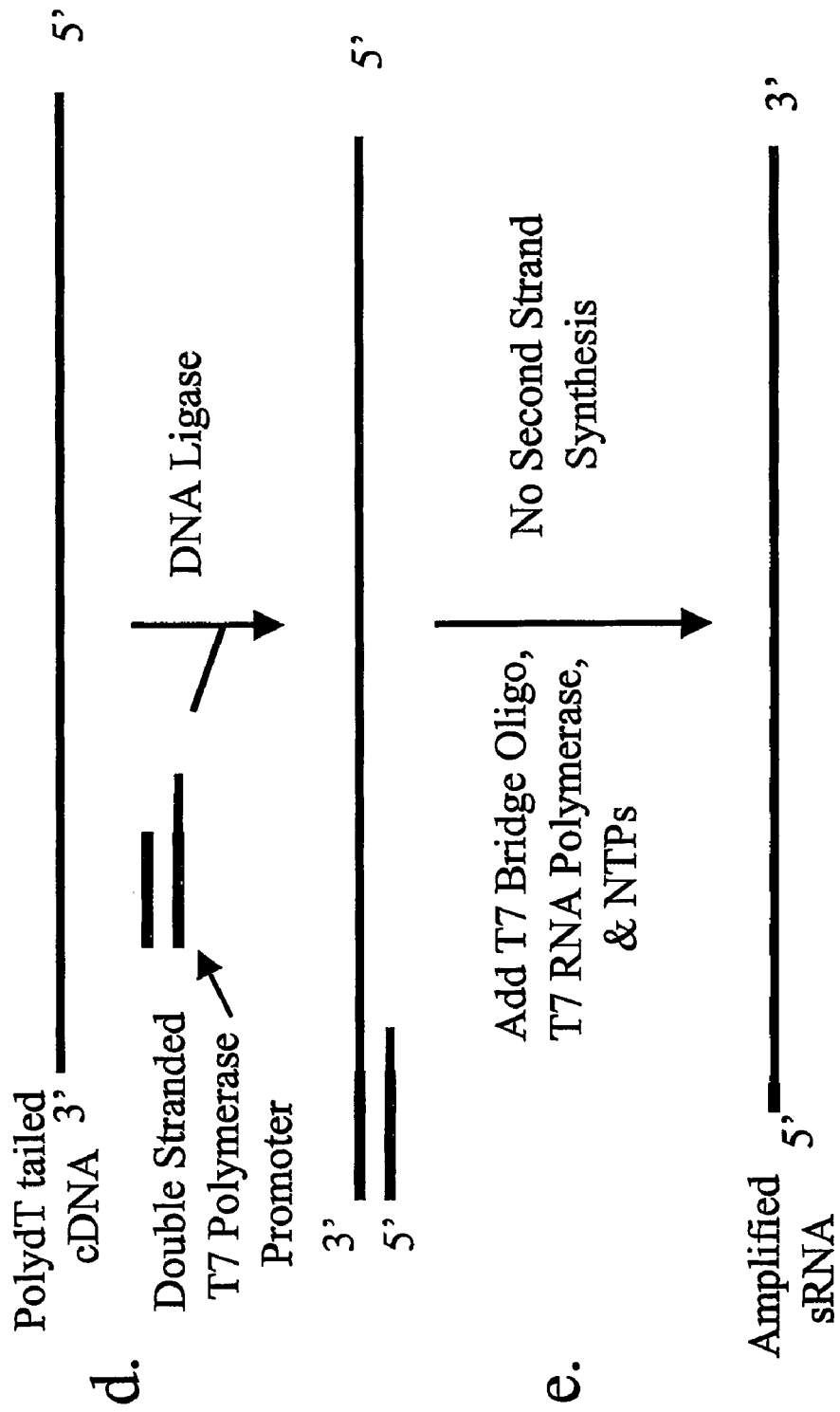

A: 123 bp Ladder
B: MessageAmp™ 1.4 µg aRNA
C: MessageAmp™ 3.5 µg aRNA
D: MessageAmp™ 7.0 µg aRNA
E: SenseAmp 1.5 µg sRNA
F: SenseAmp 2.5 µg sRNA
G: SenseAmp 6.0 µg sRNA

A B C D E F G

METHODS FOR AMPLIFICATION OF NUCLEIC ACID SEQUENCES USING STAGGERED LIGATION

PRIORITY

This application claims the benefit of U.S. Provisional Application 60/469,383, filed May 9, 2003, the disclosure of which is fully incorporated herein by reference.

BACKGROUND ART

Microarray technology has become a powerful tool for generating and analyzing gene expression profiles. Microarray expression analysis, however, generally demands large amounts of RNA that are often not available (see Wang et al., *BioTechniques* 34:394-400 (2003)). Several RNA amplification techniques have been developed to overcome this problem. These techniques, however, generally suffer from a phenomenon known as amplification bias (see, e.g., U.S. Pat. No. 6,582,906). In these cases, the amplified population of RNA molecules does not proportionally represent the population of RNA molecules existing in the original sample.

For example, in the method disclosed by Eberwine and colleagues (see, e.g., U.S. Pat. Nos. 5,545,522; 5,716,785; 5,891,636; 5,958,688; and 6,291,170), a compound oligonucleotide is utilized for the amplification, wherein the compound oligonucleotide is provided with both a T7 promoter and a primer. A cDNA copy is created of an initial mRNA transcript using the compound oliognucleotide, with subsequent second strand synthesis to create a cDNA that is double stranded. RNA amplification is conducted via the promoter portion of the compound oligonucleotide, with transcription proceeding off of the cDNA's second strand. Since the second strand is used for transcription, the Eberwine method produces amplified RNA that is antisense to the initial mRNA sequence.

The Eberwine method, however, introduces a 3' bias during each of its steps due to the incomplete processivities (i.e., the inability of an enzyme to remain attached to a nucleic acid molecule) of the enzymes utilized and the positioning of the RNA polymerase promoter (see, e.g., U.S. Pat. No. 6,582,906 and U.S. Patent Publication No. US2003/0104432). For example, the compound oligonucleotide used to produce first strand cDNA places the promoter at the 5' end of the cDNA, which corresponds to the 3' end of the message. This coupled with the inability of RNA polymerase to complete transcription of some templates (due perhaps to long polyA tail regions or interference from secondary and tertiary structures in the template) can result in a 3' bias in the amplified antisense RNA population. In addition, if second strand cDNA synthesis by DNA polymerase is incomplete, these cDNAs will lack functional promoters, resulting in a reduced representation of the original RNA molecule (or possibly a complete absence) in the amplified population.

Several RNA amplification techniques have been developed to overcome the problem of 3' bias. For example, U.S. Patent Publication No. US2003/0104432 discloses a method for amplifying sense RNA (sRNA) wherein a single stranded or double stranded bacteriophage promoter primer is ligated to the 3' end of a first strand cDNA molecule using T4 DNA or RNA ligase. Following second strand cDNA synthesis, in vitro transcription off the promoter is used to produce sense RNA molecules. A drawback of this method, however, is that ligation of blunt-end nucleic acid molecules is inefficient and must be performed at reduced incubation temperatures (see Sambrook et al., *Molecular Cloning, A Laboratory Manual* (3d ed. 2001). As such, some cDNAs will lack functional promoter primers, resulting in a reduced representation of the original RNA molecule (or possibly a complete absence) in the amplified population following in vitro transcription.

SUMMARY OF THE INVENTION

Applicants have invented methods for the production of sense RNA (sRNA) molecules from nucleic acid templates, wherein a double stranded RNA polymerase promoter is attached to the 3' end of a first strand cDNA in a staggered (also known as "sticky-end") ligation reaction. Applicants have discovered that attaching a promoter to the 3' end of a first strand cDNA via a staggered ligation reaction is more efficient than attachment via a blunt-end ligation reaction, resulting in the production of sRNA molecules that better reflect the relative abundance of each mRNA transcript in a mixture of mRNA transcripts than those obtained by prior art methods.

One aspect of the present invention is directed to a method for producing a sRNA molecule, comprising: providing a single stranded cDNA molecule having 5' and 3' ends; attaching an oligodeoxynucleotide tail onto the 3' end of the single stranded cDNA molecule; providing a double stranded RNA polymerase promoter having a sense strand and antisense strand, wherein the sense strand comprises a single stranded 3' overhang comprising a sequence complementary to the oligodeoxynucleotide tail; annealing the double stranded RNA polymerase promoter to the oligodeoxynucleotide tail by complementary base pairing with the 3' overhang sequence; ligating the 5' end of the antisense strand of the double stranded RNA polymerase to the 3' end of the oligodeoxynucleotide tail; and initiating RNA transcription using an RNA polymerase which recognizes the double stranded RNA polymerase promoter, thereby producing a sRNA molecule.

Applicants have also invented kits for the production of sense RNA molecules from nucleic acid templates, wherein a double stranded RNA polymerase promoter is attached to the 3' end of a first strand cDNA in a staggered ligation reaction.

Thus, another aspect of the present invention is directed to a kit for producing at least one sRNA molecule, comprising: a double stranded RNA polymerase promoter having a sense strand that comprises a single stranded 3' overhang sequence; and instructional materials for producing sRNA molecules using the double stranded promoter. In some embodiments, the kit further comprises at least one enzyme for attaching an oligodeoxynucleotide tail onto the 3' end of a single stranded cDNA molecule, wherein the oligodeoxynucleotide tail is complementary to the single stranded 3' overhang sequence of the double stranded RNA polymerase promoter; and at least one enzyme for ligating the double stranded promoter onto the 3' end of the cDNA molecule.

BRIEF DESCRIPTION OF THE DRAWINGS

FIGS. 1a-E together are a flowchart depicting an embodiment of the methods of the present invention.

DETAILED DESCRIPTION OF THE INVENTION

Figure 2:
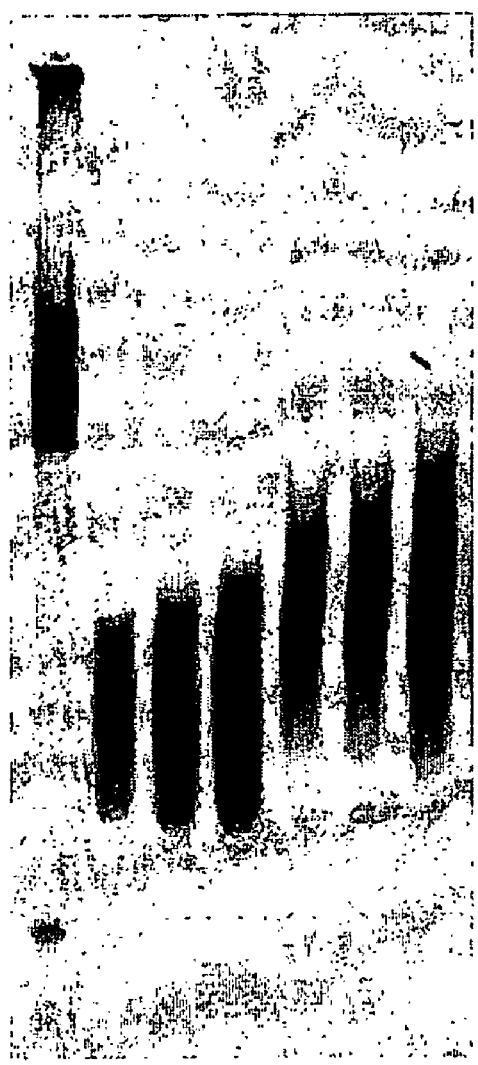
FIG. 2 is a photograph depicting various amounts of sRNA produced by the methods of the current invention visualized on a 1% agarose denaturing gel stained with ethidium bromide.

The present invention relates to methods and kits for the generation of sRNA molecules. The terms "sRNA molecule" "mRNA molecule" and "cDNA molecule" are each intended to cover a single molecule, a plurality of molecules of a single species, and a plurality of molecules of different species. The methods comprise attaching an oligodeoxynucleotide tail onto the 3' end of a single stranded cDNA molecule and ligating onto the oligodeoxynucleotide tail a double stranded promoter whose sense strand contains a single stranded 3' overhang containing a sequence complementary to the oligodeoxynucleotide tail. The use of a 3' overhang containing a sequence complementary to the 3' oligonucleotide tail properly orients the promoter and cDNA molecule for efficient staggered ligation. The resulting promoter-containing single stranded cDNA is then used in an in vitro transcription reaction with RNA polymerase to produce sRNA molecules. Such sRNA molecules represent amplified copies of the original mRNA transcript from which the single stranded cDNA was obtained.

The methods of the present invention are distinct from currently available technologies that incorporate a promoter sequence onto the 5' end of first strand cDNA molecules. In those technologies, RNA transcription proceeds in the same direction as first strand cDNA synthesis relative to the original mRNA transcript, resulting in the production of antisense RNA molecules containing a bias in favor of nucleotides proximal to the 3' polyA tail of the original mRNA transcripts. By incorporating the promoter sequence onto the 3' end of the cDNA molecules, the methods of the present invention allow genetic information at both ends of the original mRNA transcripts to be copied and amplified. The resulting sRNA molecules are more representative of the entire length of each original mRNA transcript and better reflect the relative abundance of each mRNA transcript in a mixture of. mRNA transcripts than those obtained by prior art methods.

The methods of the current invention can also be coupled with random priming without the introduction of any added priming bias. The sRNA molecules may contain polyA tails for more efficient use in downstream assays. Additionally, because the methods of the present invention utilize complementary base pairing to properly orient the promoter at the 3' end of the cDNA molecule prior to ligation, they are more efficient than those methods that attach promoters to cDNA molecules using blunt-end ligation at reduced temperatures (e.g., US2003/0104432).

The methods of the present invention rely on routine techniques in the field of molecular biology. Basic texts disclosing general molecular biology methods include Sambrook et al., *Molecular Cloning, A Laboratory Manual* (3d ed. 2001) and Ausubel et al., *Current Protocols in Molecular Biology* (1994).

Numerous methods and commercial kits for the synthesis of first strand cDNA molecules are well known in the art. Examples include the Superscript™ Double Strand cDNA Synthesis kit (Invitrogen, Carlsbad, Calif.), the Array 50™, Array 350™ and Array 900™ Detection kits (Genisphere, Hatfield, Pa.), and the CyScribe™ Post-Labelling kit (Amersham, Piscataway, N.J.). In general, high quality mRNA molecules (i.e., original mRNA transcripts) from a source of interest are used as templates in a reverse transcription reaction. The RNA may be obtained from any tissue or cell source, including virion, prokaryotic, and eukaryotic sources found in any biological or environmental sample. Preferably, the source is eukaryotic tissue, more preferably mammalian tissue, most preferably human tissue.

Any reverse transcriptase can be used in the reverse transcription reaction, including thermostable and RNase H⁻ reverse transcriptases. Preferably, an RNase H⁻ reverse transcriptase is used.

Primers for first strand cDNA synthesis are available commercially or can be synthesized and purified using techniques well known in the art. Primers for first strand cDNA synthesis include single strand oligodeoxynucleotides comprising an oligodT tail at their 3' ends that anneal to any original mRNA transcript containing a 3' polyA tail (see FIG. 1a). The tails generally range from about 10 to about 30 nucleotides in length, preferably from about 17 to about 24 nucleotides in length, and. Gene specific primers can also be used for first strand cDNA synthesis.

Alternatively, the reverse transcription reaction can be initiated using a random primer that anneals to various positions along the length of each original mRNA transcript. The primer generally ranges from about 4 to about 20 nucleotides in length, preferably from about 6 to about 9 nucleotides in length. One of ordinary skill in the art will recognize that the use of a random primer can ultimately result in the production of sRNA molecules that are better representative of the entire length of each original mRNA transcript than those produced using an oligodT primer. Additionally, the use of a random primer to generate cDNA means that RNA that would otherwise be exempt from amplification, such as degraded RNA or RNA derived from bacteria, can be used to produce amplified sRNA molecules. The random primer can be modified to include an oligodT sequence at its 5' end, generally ranging from about 10 to about 300 nucleotides in length, preferably from about 17 to about 24 nucleotides in length, such that amplified sRNA molecules produced during subsequent in vitro transcription will contain polyA tails.

Following first strand cDNA synthesis, the RNA is generally degraded prior to purification of the first strand cDNA molecules (see FIG. 1b). Any method that degrades RNA can be used, such as treatment with NaOH. Alternatively, the RNA can be left intact, with the first strand cDNA molecules purified from RNA/cDNA duplexes. Numerous methods and kits exist for the purification of DNA molecules. Examples include the MinElute™ PCR Purification kit (Qiagen, Valencia, Calif.), the SpinPrep™ PCR Clean-up kit (Novagen, Madison, Wis.), and other purification systems based on similar DNA fractionation principles.

Following first strand cDNA purification, a single stranded oligodeoxynucleotide tail is attached to the 3' end of the cDNA molecule (see FIG. 1c). The oligodeoxynucleotide tail can be incorporated by any means that attaches deoxynucleotides to single stranded DNA. Preferably, the oligodeoxynucleotide tail is attached to the single stranded cDNA using terminal deoxynucleotidyl transferase, or other suitable enzyme, in the presence of appropriate deoxynucleotides. Preferably, the oligodeoxynucleotide tail is a homopolymeric tail (i.e., polydA, polydG, polydC, or polydT). More preferably, the oligodeoxynucleotide tail is a polydT tail. The tail generally ranges from about 3 to greater than 500 nucleotides in length, preferably from about 20 to about 100 nucleotides in length.

Following attachment of the single stranded oligonucleotide tail to the 3' end of the single stranded cDNA molecule, a double stranded RNA polymerase promoter is attached to the 3' oligodeoxynucleotide tail by DNA ligation (see FIG. 1d). This is facilitated through complementary base pairing between the 3' oligodeoxynucleotide tail and an overhang sequence at the 3' end of the sense strand of the double stranded RNA polymerase promoter that contains a sequence of complementary deoxynucleotides. For example, if the oligonucleotide tail is a polydT tail, the 3' overhang of the promoter will contain a sequence of adenosine bases at its 3' end, generally ranging from about 3 to greater than 50 nucleotides in length, preferably from about 10 to about 30 nucleotides in length. The particular nucleotide sequence of the 3' overhang sequence does not have to be perfectly (i.e., 100%) complementary to the particular nucleotide sequence of the 3' oligodeoxynucleotide tail, nor does the length of the 3' overhang sequence need to be exactly equal to the length of the 3' oligodeoxynucleotide tail, for the sequences to be considered complementary to each other. Those of skill in the art will recognize that all that is required is that there be sufficient complementarity between the two sequences so that the 3' overhang can anneal to the 3' oligodeoxynucleotide tail, thus properly positioning the double stranded promoter at the 3' end of the cDNA molecule. Once properly positioned, the double stranded promoter is attached to the 3' oligonucleotide tail by ligation of the 5' end of the antisense strand of the promoter to the 3' end of the oligodeoxynucleotide tail. Such "staggered" ligation reactions are more efficient and can be performed at higher temperatures than blunt-end ligation reactions. Any DNA ligase can be used in the ligation reaction. Preferably, the DNA ligase is T4 DNA ligase.

The double stranded RNA polymerase promoter contains a sequence specifically recognized by an RNA polymerase. Any RNA polymerase can be used, so long as a specific promoter sequence is known that is recognized by the polymerase. Preferably, the promoter sequence used is recognized by a bacteriophage RNA polymerase, such as T7, T3, or SP6 RNA polymerase. An exemplary T7 polymerase promoter sense sequence is TAATACGACTCACTATAGGG (SEQ ID NO:1). An exemplary T3 polymerase promoter sense sequence is AATTAACCCTCACTAAAGG (SEQ ID NO:2). An exemplary SP6 polymerase promoter sense sequence is AATTTAAGGTGACACTATAGAA (SEQ ID NO:3).

Following attachment of the double stranded RNA polymerase promoter to the single stranded 3' oligonucleotide tail by annealing and ligation, unincorporated double stranded promoter is preferably removed by DNA purification to prevent short amplification products from being produced. In vitro transcription is then initiated by the addition of the appropriate RNA polymerase and ribonucleotides (see FIG. 1e). Such transcription can result in the production of large amounts of amplified sRNA. Methods and kits for performing in vitro transcription are well known in the art and include MEGAscript™ Transcription Kit (Ambion, Austin, Tex.) and the AmpliScribe™ High Yield Transcription kits (Epicentre Technologies, Madison, Wis.).

Although the methods of present invention are preferably performed in the absence of second strand cDNA synthesis, one of skill in the art will recognize that second strand cDNA can be optionally synthesized by extension of the 3' overhang of the sense strand of the RNA polymerase promoter using DNA polymerase in the presence of dNTPs. Preferably, the DNA polymerase is Klenow enzyme. Alternatively, second strand cDNA can be synthesized using a random primer. The random primer will anneal at various positions along the first strand cDNA and can be extended by DNA polymerase in the presence of dNTPs. These random-primed second strand cDNA fragments can be optionally ligated together to form a single second strand cDNA molecule. Such second strand cDNA molecules may stabilize (e.g., remove secondary and tertiary structure) the first strand cDNA during in vitro transcription, resulting in a higher yield of sRNA molecules.

The resulting sRNA molecules can be subjected to additional rounds of amplification using the same methodology as just described. For example, sRNA molecules produced from oligodT-mediated first strand cDNA (i.e., first round sRNA molecules) will have regenerated polyA tails at their 3' ends, which can serve as priming sites for a second round of oligodT-mediated first strand cDNA synthesis. Alternatively, a random primer can be used to reverse transcribe first strand cDNA from the first round sRNA molecules. Combinations and mixtures of oligodT and random primers can also be used for second round cDNA synthesis. A double stranded RNA polymerase promoter is then attached to the second round single stranded cDNA molecules as described above, followed by a second round of in vitro transcription with the appropriate RNA polymerase. Performing additional rounds of amplification allows smaller amounts of mRNA to be used in the initial round of amplification.

PolyA tails can be added to the 3' ends of amplified sRNA molecules that lack polyA tails (such as those produced from conventional random primed first strand cDNA) using commercially available polyA tailing kits. An example of such a kit is the Poly (A) Tailing kit (Ambion). Alternatively, polyA polymerase (available from Amersham, Invitrogen, and Ambion) combined with ATP and the amplified sRNA molecules in the appropriate buffer can be used to synthesize a polyA tail on the 3' ends of the sRNA molecules. Adding polyA tails increases the number and type of downstream assays in which the amplified sRNA molecules can be used, as well as allowing the use of more inexpensive RNA labeling alternatives in those assays.

The sRNA molecules produced by the methods of the present invention can be used for any purpose mRNA is typically used for, including gene expression studies, genetic cloning, and subtractive hybridization. For example, the sRNA molecules may be first reverse transcribed into single stranded cDNA molecules using random primers, oligodT primers, or combinations thereof. The reverse transcription reaction can be performed in the presence of detectably labeled nucleotides, such as fluorescently labeled nucleotides. Such nucleotides include nucleotides labeled with Cy3 and Cy5. Alternatively, the cDNA molecules are labeled post-synthesis by attaching at least one detectable label to the cDNA molecules. Preferably, the cDNA molecules are labeled using 3DNA™ technology (Genisphere). These dendritic reagents are further described in Nilsen et al., *J. Theor. Biol.*, 187: 273-284 (1997); Stears et al., *Physiol. Genomics*, 3: 93-99 (2000); and in U.S. Pat. Nos. 5,175,270; 5,484,904; 5,487,973; 6,072,043; 6,110,687; and 6,117,631.

The labeled single stranded cDNA molecules produced from the sRNA molecules of the present invention are useful as probes for gene expression studies. The cDNA molecules can be contacted with a nucleic acid microarray containing complementary polynucleotides. Preferably, the microarray is a GeneChip® microarray (Affymetrix, Santa Clara, Calif.). Because the sRNA molecules produced by the present methods are more representative of the entire length of each original mRNA transcript and better reflect the relative abundance of each original mRNA transcript, the results obtained for gene expression studies may be more meaningful (e.g., accurate) than those obtained using prior nucleic acid amplification techniques.

The present invention also provides kits to facilitate practice of the methods described herein. Such kits can be used in various research and diagnostic applications. For example, methods and kits of the present invention can be used to facilitate a comparative analysis of expression of one or more genes in different cells or tissues, different subpopulations of the same cells or tissues, different physiological states of the same cells or tissue, different developmental stages of the same cells or tissue, or different cell populations of the same tissue. Such analyses can reveal statistically significant differences in the levels of gene expression, which, depending on the cells or tissues analyzed, can then be used to facilitate diagnosis of various disease states.

A variety of kits may be prepared according to present invention. For example, a kit may include a double stranded RNA polymerase promoter, wherein the sense strand of the double stranded promoter comprises a single stranded 3' overhang sequence, and instructional materials for generating sRNA molecules using the double stranded promoter. While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

The kits of the present invention may further include one or more of the following components or reagents: a reverse transcriptase; an RNase inhibitor; an enzyme for attaching an oligodeoxynucleotide tail onto the 3' end of single stranded cDNA molecules, wherein the oligodeoxynucleotide tail is complementary to the single stranded 3' overhang sequence of the double stranded RNA polymerase promoter (e.g., terminal deoxynucleotide transferase); an enzyme for ligating the double stranded RNA polymerase promoter onto the 3' ends of single stranded cDNA molecules (e.g., T4 DNA ligase); an enzyme for optionally synthesizing second strand cDNA (e.g., Klenow enzyme); and an RNA polymerase that recognizes the promoter (e.g., T7 RNA polymerase). The kits may further include buffers, primers (e.g., oligodT primers, random primers), nucleotides, labeled nucleotides, RNase-free water, containers, vials, reaction tubes, and the like compatible with the generation of sRNA molecules according to the methods of the present invention. The components and reagents may be provided individually or in combination in containers with suitable storage media.

Specific embodiments according to the methods of the present invention will now be described in the following examples. The examples are illustrative only, and are not intended to limit the scope of the invention in any way.

EXAMPLES

Example 1

First Strand cDNA Synthesis

To synthesize first strand cDNA, 1-10 μl total rat brain RNA (up to 1 μg), purified using the RNAqueous® kit (Ambion), was mixed with 2 μl oligodT$_{24}$ primer (50 ng/μl) (5'-TTT TTT TTT TTT TTT TTT TTT TTT-3'; SEQ ID NO:4) and brought up to 11 μl with RNase-free water. The RNA/primer mixture was heated at 80° C. for 10 minutes and immediately cooled on ice for 1-2 min. The mixture was then mixed with 9 μl of a master mixture solution to bring the final volume to 20 μl containing 50 mM Tris-HCl (pH 8.3), 75 mM KCl, 3 mM MgCl$_2$, 10 mM dithiothreitol (DTT), 0.5 mM each dNTP, 10 U Superase-In™ (Ambion), and 200 U Superscript™ II reverse transcriptase (Invitrogen). The mixture was briefly centrifuged and incubated at 42° C. for 2 hrs. The reaction was stopped by addition of 3.5 μl 0.5 M NaOH/50 mM EDTA and heating at 65° C. for 15 min. Following brief centrifugation, the reaction was neutralized with 5 μl 1 M Tris-HCl, pH 7.5 and adjusted to 50 μl with 1× TE, pH 8.0. The reaction was purified using the MinElute™ PCR Purification Kit (Qiagen) according to the manufacturer's protocol. The first strand cDNA molecules were eluted with 10 μl EB buffer provided by the manufacturer.

Tailing of First Strand cDNA

The first strand cDNA molecules were heated at 80° C. for 10 minutes and immediately cooled on ice for 1-2 min. The cDNA molecules in 10 μl were then mixed with 15 μl of a master mixture solution to bring the final volume to 25 μl containing 6.5 μl RNase-free water, 1× tailing buffer (10 mM Tris-HCl, pH 7.0, 10 mM MgCl$_2$), 1.5 mM dTTP, and 30 U terminal deoxynucleotidyl transferase (Invitrogen). The mixture was briefly centrifuged and incubated at 37° C. for 30 min. The reaction was stopped by heating at 65° C. for 15 min and cooling at room temperature for 1-2 min (this step can be omitted if proceeding directly to the heating step of the ligation reaction below).

Ligation of T7 Promoter

The oligodT-tailed cDNA molecules were heated at 95-100° C. for 10 min and immediately cooled on ice for 1-2 min. A 1:5 dilution of 6× ligation mix was prepared by combining 4 parts ligation mix dilution buffer (395 mM Tris-HCl, pH 7.5, 30 mM MgCl$_2$, 30 mM ATP) with 1 part 6× ligation mix. The diluted 6× ligation mix contains a 5' phosphorylated T7 Ligation Oligo (7 ng/μl) (5'-CCC TAT AGT GAG TCG TAT TA-3'; SEQ ID NO:5) and a T7 dA Bridge Oligo (13.1 ng/μl) (5'-TAA TAC GAC TCA CTA TAG GGA AAA AAA AAA-3'; SEQ ID NO:6) in 395 mM Tris-HCl, pH 7.5, 30 mM MgCl$_2$, 30 mM ATP. The two oligos, when annealed together, form the double stranded T7 promoter with a 3' polydA sense strand overhang. The tailed cDNA molecules in 25 μl were then mixed with 5 μl diluted 6× ligation mix and 2 μl (2 U) T4 DNA ligase (Invitrogen). The mixture was briefly centrifuged and incubated at 23° C. for 30 min. The reaction was stopped by adding 3.5 μl 0.5 M EDTA and heating to 65° C. for 10 min. The reaction was adjusted to 50 μl with 1× TE, pH 8.0. The reaction was purified using the MinElute™ PCR Purification Kit according to the manufacturer's protocol. The T7 promoter-ligated cDNA molecules were eluted with 10 μl EB buffer.

In Vitro Transcription

Two μl of the T7 dA Bridge Oligo (50 ng/μl) (SEQ ID NO:6) was added to the T7 promoter-ligated cDNA molecules and the volume adjusted to 16 μl with RNase-water. The mixture was heated at 95° C. for 10 min and immediately iced for 2 min. The mixture was then heated at 37° C. for 10-15 min and then mixed with 24 μl of a master mixture solution to bring the final volume to 40 μl containing 1× reaction buffer, 5 mM each rNTP, and 2 μl T7 RNA polymerase (MEGAscript™ Transcription kit, Ambion). The mixture was briefly centrifuged and incubated in a 37° C. heat block for 5 min, followed by incubation in an air hybridization oven at 37° for 6-14 hrs. The amplified sRNA molecules were purified using Rneasy® Kit according to the manufacturer's protocol. The sRNA molecules were eluted in 50 μl RNase-free water, re-eluted with the same eluate, and quantified by UV-spectrophotometry at a wavelength ratio of 260/280.

Example 2

The methodology of Example 1 was followed, but first strand cDNA synthesis was performed using a random primer instead of oligodT$_{24}$ primer. Briefly, 1-10 μl total RNA (up to 1 μg) was mixed with 2 μl random 9mer primer (250 ng/μl) (5'-NNN NNN NNN-3'; SEQ ID NO:7) and brought up to 11 μl with RNase-free water. The RNA/primer mixture was heated at 80° C. for 10 minutes and immediately cooled on ice for 1-2 min. The mixture was then mixed with 9 μl of a master mixture solution to bring the final volume to 20 μl containing 50 mM Tris-HCl (pH 8.3), 75 mM KCl, 3 mM MgCl$_2$, 10 mM dithiothreitol, 0.5 mM each dNTP, 10 U Superase-In™, and 200 U Superscript™ II reverse transcriptase. The mixture was briefly centrifuged and incubated at 42° C. for 2 hrs. The reaction was stopped by addition of 3.5 µl 0.5 M NaOH/50 mM EDTA and heating at 65° C. for 15 min. Following brief centrifugation, the reaction was neutralized with 5 µl 1 M Tris-HCl, pH 7.5 and adjusted to 50 µl with 1× TE, pH 8.0. The reaction was purified using the MinElute™ PCR Purification Kit according to the manufacturer's protocol. The first strand cDNA molecules were eluted with 10 µl EB buffer provided by the manufacturer and further processed as described in Example 1, except that the 6× T7 ligation mix was used undiluted in the ligation reaction.

Example 3

Either of the methodologies of Examples 1 and 2 was followed, but following first strand cDNA synthesis, the RNA was left intact (i.e., no base hydrolysis) prior to application of the cDNA to the MiniElute™ purification column. The first strand cDNA molecules were eluted with 10 µl EB buffer provided by the manufacturer and further processed as described in Example 1.

Example 4

PolyA tails are added to the amplified sRNA molecules produced by the random primer methodologies of Examples 2 and 3 using the Poly(A) Tailing kit (Ambion). The PolyA-tailed sRNA is converted to labeled cDNA using the Array 350™ Detection kit (Genisphere) and hybridized to microarrays by standard techniques as published in the product manual for the detection kit.

Example 5

Various amounts of sRNA produced by the above-described methods were visualized on a 1% agarose denaturing gel stained with ethidium bromide. As shown in FIG. 2, the methods of the present invention (identified as SenseAmp, lanes E-G) produced larger amplified RNA molecules as compared to a commercially available, Eberwine-based method (identified as MessageAmp™, Ambion, lanes B-D). Yields of up to ~1000-fold amplification over starting RNA samples were achieved using the present methods. Experimental data generated from a comparison of the amplified antisense RNA (aRNA) produced using MessageAmp™ and the amplified sRNA produced using the present methods indicated that the present methods were more accurate than an Eberwine-based method in maintaining the relative abundance of mRNA transcripts found in the original unamplified RNA sample. The Pearson Log correlation coefficients were 0.91 and 0.86, respectively. A perfect correlation between the unamplified and amplified samples would be reflected by a Pearson Log correlation of 1.00.

Example 6

Either of the oligodT methodologies of Examples 1 and 3 was followed, but the purified sRNA molecules were subjected to a second round of RNA amplification. Briefly, the in vitro transcription reaction containing the first round amplified sRNA molecules were eluted from the Rneasy® column in 30 µl RNase-free water and re-eluted with the same eluate. The eluate was mixed with 1 µl oligodT$_{24}$ primer (50 ng/µl) (SEQ ID NO:4) and 2 µl random 9mer primer (25 ng/µl) (SEQ ID NO:6) and brought up to 37 µl with RNase-free water. The RNA/primer mixture was heated at 80° C. for 10 minutes and immediately cooled on ice for 1-2 min. The mixture was then mixed with 23 µl of a master mixture solution to bring the final volume to 60 µl containing 50 mM Tris-HCl (pH 8.3), 75 mM KCl, 3 mM MgCl$_2$, 10 mM dithiothreitol (DTT), 0.33 mM each dNTP, 10 U Superase-In™, and 200 U Superscript™ II reverse transcriptase. The mixture was briefly centrifuged and incubated at 42° C. for 2 hrs. The reaction was adjusted to 100 µl with 1× TE, pH 8.0. The reaction was purified using the MinElute™ PCR Purification Kit according to the manufacturer's protocol. The first strand cDNA molecules were eluted with 10 µl EB buffer provided by the manufacturer and further processed as described in Example 1.

Example 7

A kit for the production of sRNA molecules is assembled with the following components:
OligodT$_{24}$ Primer (50 ng/µl);
Random 9mer Primer (250 ng/µl) dNTP Mix (10 mM each);
Superase-In™ (Ambion);
dTTP Tailing Mix (10 mM);
10× Tailing Buffer (100 mM Tris-HCl, pH 7.0, 100 mM MgCl$_2$);
Terminal Deoxynucleotidyl Transferase (15-30 U/µl);
6× Ligation Mix containing a 5' phosphorylated T7 Ligation Oligo (35 ng/µl) and a T7 dA Bridge Oligo (65.6 ng/µl) in 395 mM Tris-HCl, pH 7.5, 30 mM MgCl$_2$, 30 mM ATP;
Ligation Mix Dilution Buffer (395 mM Tris-HCl, pH 7.5, 30 mM MgCl$_2$, 30 mM ATP);
T7 dA Bridge Oligo (50 ng/µl);
T4 DNA Ligase (1 U/µl); and
Nuclease-Free Water.

The components are placed in numbered vials and placed in a container with a printed instruction manual for the production of amplified sRNA molecules using the kit components. The kit can optionally contain Klenow enzyme (7.5 U/µl) if second strand cDNA synthesis is desired.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. A method for producing a sense RNA molecule, comprising:
   providing a single stranded cDNA molecule having 5' and 3' ends;
   attaching an oligodeoxynucleotide tail to the 3' end of said single stranded cDNA molecule;
   providing a double stranded RNA polymerase promoter having a sense strand and antisense strand, wherein the sense strand comprises a single stranded 3' overhang comprising a sequence complementary to said oligodeoxynucleotide tail;
   annealing said double stranded RNA polymerase promoter to said oligodeoxynucleotide tail by complementary base pairing with said 3' overhang sequence;
   ligating the 5' end of the antisense strand of said double stranded RNA polymerase promoter to the 3' end of said oligodeoxynucleotide tail; and initiating RNA transcription using an RNA polymerase which recognizes said double stranded promoter, thus producing a sense RNA molecule (sRNA).

2. The method of claim 1, wherein said attaching comprises providing a mRNA transcript having 5' and 3' ends; and synthesizing a single stranded cDNA molecule from said mRNA transcript.

3. The method of claim 2, wherein synthesis of the single stranded cDNA molecule comprises reacting the mRNA transcript with a RNase H- reverse trancriptase.

4. The method of claim 2, wherein synthesis of the single stranded cDNA molecule comprises reacting the mRNA transcript with an oligodT primer.

5. The method of claim 2, wherein synthesis of the single stranded cDNA molecule comprises reacting the mRNA transcript with a random primer.

6. The method of claim 2, further comprising purifying the single stranded cDNA molecule prior to attaching the oligodeoxynucleotide tail.

7. The method of claim 6, further comprising degrading the mRNA transcript prior to purifying the single stranded cDNA molecule.

8. The method of claim 6, wherein the mRNA transcript is not degraded prior to purifying the single stranded cDNA molecule.

9. The method of claim 1, wherein the oligodeoxynucleotide tail is a homopolymeric tail.

10. The method of claim 9, wherein the homopolymeric tail is a polydT tail.

11. The method of claim 1, wherein the oligodeoxynucleotide tail is attached to the 3' end of the single stranded cDNA molecule using terminal deoxynucleotidyl transferase.

12. The method of claim 1 or 2, wherein the double stranded RNA polymerase promoter is a T7, T3, or SP6 promoter.

13. The method of claim 12, wherein the double stranded RNA polymerase promoter is a T7 promoter.

14. The method of claim 1, wherein the single stranded 3' overhang comprises a sequence of adenosine bases.

15. The method of claim 1, wherein ligation is performed using T4 DNA ligase.

16. The method of claim 1, wherein RNA transcription is initiated using T7 RNA polymerase.

17. The method of claim 1, further comprising synthesizing second strand cDNA prior to initiating RNA transcription.

18. The method of claim 17, wherein the second strand cDNA is synthesized using DNA polymerase.

19. The method of claim 17, wherein the second strand cDNA is synthesized by extension of the 3' overhang of the sense strand of the RNA polymerase promoter.

20. The method of claim 17, wherein the second strand cDNA is synthesized using a random primer, thus producing random-primed second strand cDNA fragments.

21. The method of claim 20, wherein the random-primed second strand cDNA fragments are ligated together prior to initiating RNA transcription.

22. The method of claim 1, further comprising amplifying the resulting sRNA molecule.

23. The method of claim 22, wherein the sRNA amplification is initiated using a combination of oligodT and random primers.

24. The method of claim 1, wherein the resulting sRNA molecule comprises a polyA tail.

25. The method of claim 24, wherein the polyA tail is attached using polyA polymerase.

26. The method of claim 1, further comprising reverse transcribing the resulting sRNA molecule, thereby producing a single stranded cDNA molecule.

27. The method of claim 26, wherein the reverse transcription comprises incorporating detectably labeled nucleotides into the single stranded cDNA molecule.

28. The method of claim 27, wherein the detectably labeled nucleotides comprise a fluorescent dye.

29. The method of claim 28, wherein the fluorescent dye is cy3 or cy5.

30. The method of claim 26, further comprising attaching at least one detectable label to the resulting cDNA molecule.

31. A method for probing a nucleic acid microarray, comprising contacting a nucleic acid microarray with detectably labeled cDNA, wherein said detectably labeled cDNA is prepared by the following steps:
providing a single stranded cDNA molecule having 5' and 3' ends;
attaching an oligodeoxynucleotide tail to the 3' end of said single stranded cDNA molecule;
providing a double stranded RNA polymerase promoter having a sense strand and antisense strand, wherein the sense strand comprises a single stranded 3' overhang comprising a sequence complementary to said oligodeoxynucleotide tail;
annealing said double stranded RNA polymerase promoter to said oligodeoxynucleotide tail by complementary base pairing with said 3' overhang sequence;
ligating the 5' end of the antisense strand of said double stranded RNA polymerase promoter to the 3' end of said oligodeoxynucleotide tail;
initiating RNA transcription using an RNA polymerase which recognizes said double stranded promoter, thus producing a sense RNA molecule (sRNA); and
reverse transcribing a resulting sRNA molecule, thereby producing a single stranded cDNA molecule, wherein the reverse transcribing comprises incorporating detectably labeled nucleotides into the single stranded cDNA molecule.

32. The method of claim 2, wherein the mRNA transcript is of mammalian origin.

33. The method of claim 2, wherein the mRNA transcript is of human origin.

34. The method of claim 2, wherein the mRNA transcript is isolated from a biological source comprising degraded RNA.

35. A kit for producing at least one sRNA molecule, comprising: a double stranded RNA polymerase promoter having a sense strand and antisense strand, wherein the sense strand of said double stranded RNA polymerase promoter comprises a single stranded 3' overhang sequence; instructional materials for generating sRNA molecules using said double stranded promoter; at least one enzyme for attaching an oligodeoxynucleotide tail onto the 3' end of a single stranded cDNA molecule, wherein the oligodeoxynucleotide tail is complementary to the single stranded 3' overhang sequence of said double stranded RNA polymerase promoter; and at least one enzyme for ligating said double stranded promoter onto the 3' end of said cDNA molecule.

36. The kit of claim 35, wherein said enzyme for attaching is terminal deoxynucleotidyl transferase and wherein said enzyme for ligating is T4 DNA ligase.

37. The kit of claim 36, further comprising an oligodT primer; a random primer; dNTPs; and a RNase inhibitor.

38. The kit of claim 37, further comprising a DNA polymerase.

* * * * *